United States Patent [19]

Boulet et al.

[11] 4,173,710
[45] Nov. 6, 1979

[54] HALOGENATED POLYETHER POLYOLS AND POLYURETHANE FOAMS PRODUCED THEREFROM

[75] Inventors: Jean-Claude Boulet, Tavaux-Cite, France; Rene Walraevens, Brussels, Belgium; Gerard Bonnety, Tavaux-Cite, France; Jacques Lolivier; Paul Trouillet, both of Brussels, Belgium

[73] Assignee: Solvay & Cie, Brussels, Belgium

[21] Appl. No.: 851,252

[22] Filed: Nov. 14, 1977

Related U.S. Application Data

[60] Continuation of Ser. No. 729,423, Oct. 4, 1976, abandoned, which is a division of Ser. No. 607,595, Aug. 25, 1975, abandoned, which is a continuation of Ser. No. 353,536, Apr. 23, 1973, abandoned.

[30] Foreign Application Priority Data

May 15, 1972 [LU] Luxembourg ............................ 65359
Feb. 12, 1973 [LU] Luxembourg ............................ 67005

[51] Int. Cl.² ...................... C07C 43/02; C07C 43/12; C08J 9/00
[52] U.S. Cl. .................................. 568/614; 568/674; 568/676; 521/174; 521/126; 521/129
[58] Field of Search .................. 260/615 R, 615 B; 568/614, 674, 676

[56] References Cited

U.S. PATENT DOCUMENTS

| | | | |
|---|---|---|---|
| 1,875,312 | 8/1932 | Yohtz | 260/635 E |
| 2,135,271 | 11/1938 | Bakar | 260/635 E |
| 2,236,919 | 4/1941 | Reynhart | 260/615 B X |
| 2,575,558 | 11/1951 | Hewey et al. | 260/615 B |
| 2,581,464 | 1/1952 | Zech | 260/615 B |
| 3,475,499 | 10/1969 | Winnick | 260/615 B X |
| 3,576,890 | 4/1971 | Binning | 260/635 E |

FOREIGN PATENT DOCUMENTS 1350425  12/1963  France ................................ 260/615 B

*Primary Examiner*—Howard T. Mars
*Attorney, Agent, or Firm*—Larson, Taylor and Hinds

[57] ABSTRACT

New halogenated polyether polyols for the production of permanently fire-proof polyurethane foams, said halogenated polyether polyols corresponding to the general formula:

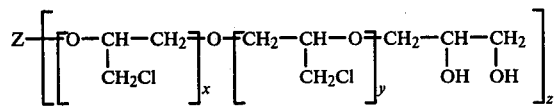

in which z represents a number between 2 and 6, x and y represent numbers between 0 and 12 such that the mean value x+y per chain is between 0 and 12, and that z (x+y), in which x+y represents the mean value of x+y in the entire molecule, is between 1 and 72, and Z represents the residue of a halogenated polyhydroxyl compound initiator and comprises a $C_2$ to $C_6$ halogenated aliphatic radical of valence z, the halogen being selected from the group consisting of chlorine and bromine.

6 Claims, No Drawings

HALOGENATED POLYETHER POLYOLS AND POLYURETHANE FOAMS PRODUCED THEREFROM

This is a continuation, of application Ser. No. 729,423 now abandoned filed Oct. 4, 1976 which is a divisional of Ser. No. 607,595 filing date Aug. 25, 1975 now abandoned which in turn is a cont. of Ser. No. 353,536 filed Apr. 23, 1973 now abandoned.

The present invention relates to new halogenated polyether polyols and also to polyurethane foams produced therefrom.

It is known that rigid polyurethane foams have many varied uses in industry, particularly in the fields of building and insulation, where resistance to fire is a desirable or even indispensable property.

Various means exist for imparting fire-resisting properties to polyurethane foams. A well known process consists of the incorporation in the foams of fireproofing additives, such as antimony oxide or else halogenated and/or phosphorus compounds, such as tris(dibromopropyl) or tris(dichloropropyl) phosphates, chlorinated biphenyls and halogenated hydrocarbons. These additives, which are not chemically bonded to the base polymer, are incapable of providing uniformly distributed permanent resistance to fire. Moreover, they generally have a plasticising effect on the foam, and consequently impair its mechanical properties, particularly its compressive strength and dimensional stability.

Another means of producing fire-resisting polyurethane foams consists in using halogenated and/or phosphorated polyols.

In French Pat. No. 1,350,425 of 12.3.1963 in the name of Olin Mathieson Corp there is described the use of halogenated polyether polyols produced by adding epihalohydrins to monomeric polyhydric alcohols containing at least two hydroxyl groups. This addition reaction yields halogenated polyether polyols having a number of secondary hydroxyl functions equal to the number of hydroxyl functions of the starting hydroxyl reactant. The cellular polyurethanes resulting from the reaction of organic polyisocyanates on these halogenated polyether polyols certainly have satisfactory permanent fire-resisting properties, but their dimensional stability is generally inadequate. Moreover, their production is difficult because of the low reactivity of these polyether polyols; this reactivity is still poorer than that of the corresponding non-halogenated polyether polyols.

The Applicants have now found new halogenated polyether polyols which in particular permit the production of permanently fireproof polyurethane foams.

The halogenated polyether polyols according to the invention correspond to the general formula:

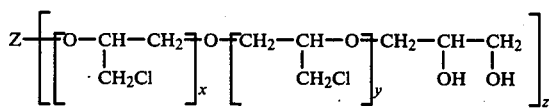

in which z represents a number between 2 and 6, x and y represent numbers between 0 and 12 such that the mean value $\overline{x+y}$ per chain is between 0 and 12 and that z $\overline{(x+y)}$, in which $\overline{x+y}$ represents the mean value of x+y in the entire molecule, is between 1 and 72, and Z represents an organic radical of valence z.

The chlorinated polyether polyols according to the invention are characterised by the presence of α-diol groups; they contain primary and secondary hydroxyl groups which are not deactivated by the immediate proximity of chlorine atoms.

Because of their special properties, the halogenated polyether polyols according to the invention have numerous different applications, such as the production of alkyde resins and additives for epoxy resins. The polyether polyols are also suitable for the production of chlorinated and phosphorated polyether polyols by reaction with organic and/or inorganic phosphorus compounds suchas phosphorous, phosphoric, pyro- and polyphosphoric acids, mono- and diphosphonic acids and their esters.

It has in particular been found that the halogenated polyether polyols according to the invention are suitable for the production of rigid and semi-rigid fire-resisting polyurethane foams. The invention likewise relates to a process for the production of rigid or semi-rigid fire-resisting polyurethane foams. According to this process, rigid or semi-rigid fireproof polyurethane foams are produced by the reaction of an organic polyisocyanate and at least one polyether polyol of the general formula:

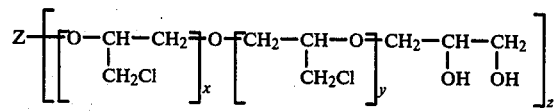

in which z represents a number between 2 and 6, x and y represent numbers between 0 and 12 such that the mean value $\overline{x+y}$ per chain is between 0 and 12 and that z $\overline{(x+y)}$, in which $\overline{x+y}$ represents the mean value of x+y in the entire molecule, is between 1 and 72, and Z represents an organic radical of valence z.

Chlorinated polyether polyols according to the invention which are particularly preferred for the production of rigid fireproof polyurethane foams correspond to the above general formula in which z represents a number between 2 and 6, x and y represent numbers between 0 and 4 such that the mean value $\overline{x+y}$ per chain is between 0 and 4 and that z $\overline{(x+y)}$, in which $\overline{x+y}$ represent the mean value of x+y in the entire molecule, is between 1 and 24, and Z represents a $C_2$ to $C_6$ organic radical of valence z.

Polyether polyols which are very particularly preferred for the production of rigid polyurethane foams correspond to the above general formula, in which z, x and y have the meanings defined above, and Z represents a $C_2$ to $C_6$ halogenated saturated or unsaturated aliphatic radical of valence z, the halogen being selected from the group comprising chlorine and bromine.

The halogenated polyether polyols according to the invention permit the production of fireproof polyurethane foams possessing mechanical properties similar to if not better than those of commercial non-halogenated polyether polyols.

The halogenated polyether polyols of the invention can be used alone or in mixtures for the production of polyurethanes.

The relative proportion of halogenated polyether polyols according to the invention in the mixture of polyether polyols used may vary within a fairly wide range. The self-extinguishability properties of the resulting polyurethane are obviously the better, the higher this proportion. Self-extinguishable rigid polyurethanes according to the standard ASTM D 1692 can be obtained by using polyether polyol mixtures containing one or more non-halogenated polyether polyols and 40%, preferably 70%, by weight of those polyether polyols according to the invention which have the lowest halogen content and only 20–35% by weight of those halogenated polyether polyols according to the invention which have the highest halogen content.

The rigid and semi-rigid polyurethane foams forming the object of the invention are produced in a manner known per se by reacting halogenated polyether polyols according to the invention, or mixtures of non-halogenated polyether polyols and halogenated polyether polyols according to the invention, respectively, and organic polyisocyanates in the presence of a foaming agent and of one or more reaction catalysts, optionally water, emulsifying agents, and/or stabilising agents, filling materials, pigments, etc.

The halogenated polyether polyols according to the invention are suitable for the production of polyurethane foams by any conventional foaming methods, such as the single-stage method known as "one-shot", methods utilising a prepolymer or a semi-polymer, the so-called "frothing" pre-expansion method.

All organic isocyanates normally used for the production of rigid polyurethane foams are suitable. Particularly preferred isocyanates are methylene bis(4-phenylisocyanate) in the pure or partially polymerised state, tolylene diisocyanates in the pure state or in the form of isomer mixtures, and naphthalene 1,5-diisocyanate.

The theoretical amount of polyisocyanate necessary for the production of polyurethane is calculated in known manner in dependence on the hydroxyl index of the polyether polyol or polyols and, where applicable, of the water which are present. It is advantageous to use a slight excess of polyisocyanate so as to ensure an isocyanate index of 105–120, which improves the hot distortion resistance of the resulting rigid polyurethane foam.

The catalyst used may be any of the catalysts known to be used for this purpose, particularly the tertiary amines such as triethylenediamine (1,4-diazabicyclo[2.2.2]octane), triethylamine, trimethylamine, dimethylaminoethanol, and the metallic salts, such as the salts of antimony, tin, and iron. Triethylamine is a particularly preferred catalyst.

The amount of catalyst may vary to a certain extent; it affects the mechanical properties of the resulting foam. From 0.1 to 3% by weight of catalyst, referred to the polyether polyol or mixture of polyether polyols, is generally used.

The choice of the foaming agent is not critical. Known foaming agents are all suitable without exception, particularly water, halogenated hydrocarbons such as methylene chloride and chloroform, and also the chlorofluoro alkanes such as trichloromonofluoromethane (R 11), dichlorodifluoromethane (R 12), and trichlorotrifluoroethane (R 113).

The quantity of foaming agent may also vary to a fairly great extent. It is advantageous to use from 0.1 to 10% of water and/or from 1 to 70% by weight of halogenated hydrocarbon referred to the polyether polyol or mixture of polyether polyols.

It may be advantageous to prepare the polyurethane foams by using small amounts of a surfactant which contributes towards improving the cellular structure, preferably from 0.2 to 2% by weight referred to the polyether polyol or mixture of polyether polyols.

The chlorinated polyether polyols forming the object of the invention may be obtained by oligomerisation, co-oligomerisation, condensation, dehydrochlorination, and hydrolysis, the starting materials comprising on the one hand epichlorohydrin and on the other hand water or di- or polyhydroxylated compounds which may optionally be halogenated and/or have ether oxide bonds, and/or double bonds capable of being halogenated in a subsequent stage according to techniques well known to those versed in the art.

A suitable mode of operation comprises hydrolysis in a diluted acid medium of di- or polyglycidyl ethers of epichlorohydrin oligomers of the general formula:

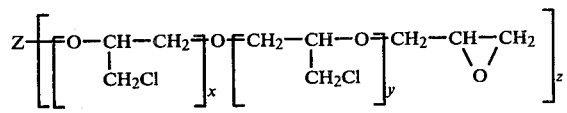

in which z is a number between 2 and 6, x and y represent numbers between C and 12 such that the mean value $\overline{x+y}$ per chain is between 0 and 12 and that z $\overline{(x+y)}$, in which $\overline{\overline{x+y}}$ represents the mean value of $x+y$ in the entire molecule, is between 1 and 72, and Z represents an optionally halogenated saturated or unsaturated organic radical of valence z.

This hydrolysis may be accompanied by secondary condensation reactions which lead to a lengthening of the chains with the formation of chlorinated polyether polyols containing more chlorine and less hydroxyl functions.

It is not indispensable to separate these products, which are likewise chlorinated polyether polyols containing α-diol groups, the presence of which is not in any way harmful to the synthesis of further processed products.

The hydrolysis of di- and polyglycidyl ethers of epichlorohydrin oligomers is advantageously effected in a nitric or perchloric acid medium.

The amounts of water and acid to be used for the hydrolysis may vary to a considerable extent. They govern in particular the reaction period and also the rate of the secondary condensation reactions. It is advantageous to use from $1.2 \times 10^{-2}$ to $2.5 \times 10^{-2}$ moles of nitric acid and from 1 to 10 kg of water per mole of di- or polyglycidyl ether.

The hydrolysis reaction is carried out with agitation at the boiling temperature of the reaction medium. The end of the reaction is detected by determination of the residual oxirannic oxygen.

After cooling, the reaction product may be in the form of a two-phase system, comprising an aqueous phase containing the chlorinated polyether polyols which are the lightest and have the most hydroxyl functions, and a dense water-saturated organic phase containing the halogenated polyether polyols which are the heaviest and contain the most halogen. It is not indispensable to separate these two phases and to treat them separately in order to isolate the polyether polyols which they contain.

The mode of operation described above is suitable for the production of polyether polyols halogenated "to measure" which have variable relative contents of halogen and hydroxyl functions which are determined by appropriate choice of the initial glycidyl ether and/or of the hydrolysis conditions.

The di- and polyglycidyl ethers of epichlorohydrin oligomers are obtained, in a manner known per se, by dehydrochlorination in an alkaline medium of chlorinated polyether polyols having end chlorohydrin groups resulting from the oligomerisation of epichlorohydrin which is initiated by water or a di- or polyhydroxyl compound, which may be saturated or unsaturated, halogenated or non-halogenated, and of an aliphatic, alicyclic, or aromatic nature.

A first type of di- and polyglycidyl ethers according to the formula above comprises those the formula of which contains a non-halogenated radical Z. They are obtained by dehydrochlorination of chlorinated polyether polyols resulting from the catalytic oligomerisation of epichlorohydrin which is initiated by saturated or unsaturated polyols, such as ethyleneglycol, propyleneglycol, and hexamethyleneglycol, glycerine, butanetriol and hexanetriol, trimethylolpropane, erythritol and pentaerythritol, mannitol and sorbitol, resorcinol, catechol, hydroquinone, bisphenol A, di- and tri-ethyleneglycol, di- or tri-propyleneglycol, 2-butene-1,4-diol, 3-butene-1,2-diol, 2-butyne-1,4-diol, 3-butyne-1,2-diol, 1,5-hexadiene-3,4-diol, 2,4-hexadiene-1,6-diol, 1,5-hexadiyne-3,4-diol, 2,4-hexadiyne-1,6-diol.

The polyols which are particularly preferred are the aliphatic polyols, particularly 2-butene-1,4-diol and 2-butyne-1,4-diol, ethylene glycol, and glycerine. The use of these last-mentioned initiators leads to the obtaining of di- and polyglycidyl ethers corresponding to the general formula given above in which Z represents the radicals —CH$_2$—CH$_2$— and

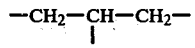

respectively.

A second type of di- and polyglycidyl ethers leading to polyester polyols having a higher halogen content comprises those of which the formula given above contains a halogenated radical Z, the halogen being selected from the group comprising chlorine and bromine. They may be obtained by the dehydrochlorination of the chlorinated polyether polyols resulting from the catalytic oligomerisation of epichlorohydrine which is initiated by saturated or unsaturated halogenated polyols, such as glycerol monochloro- and monobromohydrins, 3,4-dibromo-1,2-butanediol, 2,3-dibromo-1,4-butanediol, the 2,3-dibromo-2-butene-1,4-diols, the 3,4-dibromo-2-butene-1,2-diols, 2,2(bis)-bromomethyl-1,3-propanediol, 1,2,5,6-tetrabromo-3,4-hexanediol.

The oligomerisation of epichlorohydrin may also be initiated by a mixture of brominated and/or unsaturated diols.

The molar ratio of epichlorohydrin and iniator polyol is not critical and may vary within a wide range. This ratio governs the hydroxyl index of the resulting polyether polyol.

The oligomerisation catalyst may be any of the acid catalysts known for this type of reaction. It is nevertheless preferred to use boron trifluoride in the free or complexed state.

Di- and polyglycidyl ethers of brominated epichlorohydrin oligomers can also be obtained by partial or complete molecular bromination of the di- or polyglycidyl ethers of unsaturated epichlorohydrin oligomers obtained by dehydrochlorination in an alkaline medium of the unsaturated chlorinated polyether polyols resulting from the catalytic oligomerisation of epichlorohydrin which is initiated by an unsaturated di- or polyhydroxyl compound.

Furthermore, the halogen content of the polyether polyols of the invention, and consequently the flame resistance of the polyurethanes derived therefrom, can be still further increased if these polyether polyols also have unsaturations, by partial or complete bromination of these unsaturations. By this technique the unsaturated polyols resulting from the hydrolysis in a dilute acid medium of the di- or polyglycidyl ethers of unsaturated epichlorohydrin oligomers of the general formula:

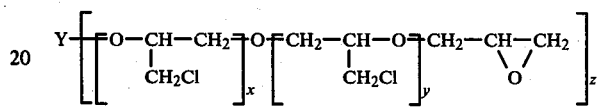

in which x, y, and z correspond to the definition given above and Y represents an unsaturated organic radical or valence z, are brominated.

The method of bromation of the polyether polyols and glycidyl ethers is not critical. It is possible to operate in a manner known per se, optionally in the presence of a catalyst and of an inert solvent such as chloroform, carbon tetrachloride, methylene chloride, or o-dichlorobenzene.

The temperature is generally kept below 50°–60° C.

The amount of bromine used is not critical. Nevertheless, it is preferred to use an almost stoichiometric quantity of bromine.

Particularly preferred polyether polyols correspond to the general formula in which Z represents the radicals

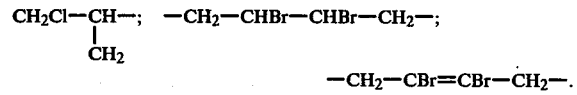

The examples given illustrate the invention, without however limiting it.

Examples 1, 2, 3, 4, and 5 relate to the production of mixtures of chlorinated polyether polyols by hydration of glycidyl ethers of epichlorohydrin oligomers obtained by adding epichlorohydrin to monochloropropanediol (Examples 1, 2, 3), ethylene glycol (Example 4) and glycerine (Example 5).

Example 6 relates to the production of chlorobrominated polyether glycols by bromination of unsaturated chlorinated polyether polyols resulting from the hydrolysis of the diglycidyl ether produced by adding epichlorohydrin to butynediol.

Examples 7 and 8 relate to polyurethane foams produced with the intervention of mixtures of chlorinated polyether polyols produced respectively in accordance with Examples 1 and 4.

Example 9 relates to polyurethane foams produced with the intervention of a mixture of chlorobrominated polyether polyols according to Example 6 and of a commercial non-halogenated polyether polyol having a hydroxyl index of 503 and a viscosity of 118 poises at 20° C. which is sold under the trade mark VORANOL RN 490.

Example 10, a reference example, relates to polyurethane foams produced with the aid of commercial polyether polyol.

Example 11, also a reference example, related to polyurethane foams produced with the aid of a chlorinated polyether polyol according to the aforesaid patent of Olin Mathieson Corp, and synthetised by oligomerisation of epichlorohydrin in the presence of glycerine in the molar ratio 4/1.

EXAMPLE 1

500 g, that is to say 1 mole, of the diglycidyl ether of epichlorohydrin tetramer, 1,000 cm$^3$ of demineralised water, and 12.5 cm$^3$ of normal nitric acid are introduced at ambient temperature into a 2-liter glass reactor immersed in a bath of oil under thermostat control and equipped with an agitator and a reflux condenser.

The medium is brought to boiling point and kept under, constant agitation. After 20 hours, determination of oxirannic oxygen indicates that all the diglycidyl ether is hydrated. The reactional mixture is then cooled and subjected just as it is, without separation of the aqueous and organic phases, to evaporation under reduced pressure so as to drive off the major part of the water. The chlorinated polyether polyols are then dried by azeotropic entrainment of water by methylene chloride. Entrainment by nitrogen at 60° C. enables the last traces of water and methylene chloride to be driven off.

A relatively viscous, clear liquid is obtained which has the following characteristics:

| | |
|---|---|
| Specific gravity, 20° C. | 1.337 |
| Viscosity at 20° C., poises | 750 |
| Chlorine content, % by weight | 25 |
| Hydroxyl index, mg KOH/g polyol | 409 |
| Gardner coloration index | 9 |
| Mean measured molecular mass | 534 |
| Mean value of ($\overline{x + y}$), calculated | 1.51 |

EXAMPLE 2

The mode of operation is similar to that of Example 1, using 500 g, that is to say 0.815 mole, of the diglycidyl ether of epichlorohydrin trimer. A clear liquid is obtained which has the following characteristics:

| | |
|---|---|
| Specific gravity, 20° C. | 1.329 |
| Viscosity at 20° C., poises | 610 |
| Chlorine content, % by weight | 24.21 |
| Hydroxyl index, mg KOH/g, polyol | 458 |
| Gardner coloration index | 6 |
| Mean measured molecular mass | 469 |
| Mean value of ($\overline{x + y}$), calculated | 1.19 |

The abovedescribed mixture of chlorinated polyether polyols produced according to Example 2 is decanted and separated into an aqueous phase and an organic phase, and the two phases are then treated separately in order to isolate the products which they contain.

The product collected in the aqueous phase, which represents 47% by weight of the total of the products collected in the aqueous and organic phases, has the following properties:

| | |
|---|---|
| Specific gravity, 20° C. | 1.320 |
| Viscosity at 20° C., poises | 410 |
| Chlorine content, % by weight | 22.65 |
| Hydroxyl index, mg KOH/g polyol | 562 |
| Gardner coloration index | 6 |
| Mean measured molecular mass | 366 |
| Mean value of ($\overline{x + y}$), calculated | 0.66 |

The product collected in the organic phase has the following properties:

| | |
|---|---|
| Specific gravity, 20° C. | 1.336 |
| Viscosity at 20° C., poises | 418 |
| Chlorine content, % by weight | 26.22 |
| Hydroxyl index, mg KOH/g polyol | 360 |
| Gardner coloration index | 6 |
| Mean measured molecular mass | 567 |
| Mean value of ($\overline{x + y}$), calculated | 1.75 |

EXAMPLE 3

The operation procedure is similar to that of Example 1, using 500 g, that is to say 1.185 moles, of the diglycidyl ether of epichlorohydrin pentamer. A clear liquid is obtained, which has the following properties:

| | |
|---|---|
| Specific gravity, 20° C. | 1.344 |
| Viscosity at 20° C., poises | 950 |
| Chlorine content, % by weight | 29.29 |
| Hydroxyl index, mg KOH/g polyol | 336 |
| Gardner coloration index | 7 |
| Mean measured molecular mass | 643 |
| Mean value of ($\overline{x + y}$), calculated | 2.12 |

EXAMPLE 4

The operating procedure is similar to that of Example 1, utilising 500 g, that is to say 1.10 mole, of the diglycidyl ether of an epichlorohydrin oligomer, produced by dehydrochlorination of the product resulting from the addition of 5 moles of epichlorohydrin to 1 mole of ethylene glycol.

A clear liquid is obtained which has the following characteristics:

| | |
|---|---|
| Specific gravity, 20° C. | 1.312 |
| Viscosity at 20° C., poises | 291 |
| Chlorine content, % by weight | 22.8 |
| Hydroxyl index, mg KOH/g polyol | 430 |
| Gardner coloration index | 6 |
| Mean measured molecular mass | 506 |
| Mean value of ($\overline{x + y}$), calculated | 1.63 |

EXAMPLE 5

The operating procedure is similar to Example 1, utilising 500 g, that is to say 0.55 mole, of the triglycidyl ether of an epichlorohydrin oligomer produced by dehydrochlorination of the product resulting from the addition of 10 moles of epichlorohydrin to 1 mole of glycerine.

A very viscous liquid is obtained which has the following characteristics:

| | |
|---|---|
| Specific gravity, 20° C. | 1.343 |
| Chlorine content, % by weight | 26.5 |
| Hydroxyl index, mg KOH/g polyol | 308 |
| Gardner coloration index | 12 |

-continued

| Mean measured molecular mass | 989 |
| Mean value of ($\overline{x + y}$), calculated | 2.59 |

EXAMPLE 6

500 g, that is to say 1.16 mole of the diglycidyl ether of an unsaturated epichlorohydrin oligomer, produced by dehydrochlorination of the product resulting from the addition of 4.5 moles of epichlorohydrin to 1 mole of butynediol, 1,000 cm³ of demineralised water, and 2.9 cm³ of a 70 weight % aqueous solution of perchloric acid are introduced at ambient temperature into a 2-liter glass reactor immersed in a bath of oil under thermostat control and equipped with an agitator and a reflux condenser.

The operating procedure is in accordance with Example 1. A brownish mobile liquid is obtained which is composed of 1.16 mole of chlorinated polyether polyol having an acetylene unsaturation.

1.16 mole of bromine is added drop by drop to the cooled reactional mixture to which 1.4 g of boron trifluoride diethyl etherate has been added. It is ensured that the temperature does not exceed 50° C. After the introduction of the bromine, which takes about 2 hours, the mixture is left under agitation until the brown vapours of the gas phase disappear. The acidity is then neutralised by adding anhydrous calcium carbonate, and the mixture is kept under vigourous agitation for 2 hours. The liberation of carbon dioxide is observed. Since the mass obtained is fairly viscous, 0.5 liter of methylene chloride is added and the product then filtered to eliminate calcium carbonate. The methylene chloride is then eliminated by evaporation at 95° C. at 15 mm mercury until the weight is constant.

The characteristics of the resulting chlorobrominated polyether polyol, which has a double bond, are as follows:

| Specific gravity, 20° C. | 1.67 |
| Viscosity at 20° C., poises | 900 |
| Chlorine content, % by weight | 14.2 |
| Bromine content, % by weight | 25.6 |
| Hydroxyl index, mg KOH/g polyol | 330 |
| Gardner coloration index | 10 |
| Mean measured molecular mass | 746 |
| Mean value of ($\overline{x + y}$), calculated | 1.9 |

EXAMPLE 7

100 g of chlorinated polyether polyols of Example 1, 0.5 g of silicone DC 193, 2 g of triethylamine, and 40 g of trichlorofluoromethane (R 11) are introduced in succession into a 400 cm³ glass container. The mixture is agitated so as to make it perfectly homogeneous. 103.8 g of crude methylene bis(4-phenylisocyanate) are then added. The resulting mixture is agitated for 20 seconds, then poured into a mould, and allowed to set at ambient temperature. The creaming time amounts to 3 seconds and the development time to 30 seconds. A self-extinguishable rigid foam is obtained of which the main physical and mechanical characteristics are shown in Table I, while its fire-resisting properties are shown in Table II.

EXAMPLE 8

The operating procedure is similar to that of Example 7, but using 100 g of the chlorinated polyether polyols of Example 4 and 109.2 g of crude methylene bis(4-phenylisocyanate). The creaming time amounts to 6 seconds and the development time to 24 seconds. A self-extinguishable rigid foam is obtained the main physical and mechanical characteristics of which are shown in Table I, while its fire-resisting properties are shown in Table II.

EXAMPLE 9

The operating procedure is similar to that of Example 7, but using 50 g of a mixture of the chlorobrominated polyether polyols of Example 6, 50 g of commercial polyether polyol, 1.5 g of triethylamine and 106 g of methylene bis(4-phenylisocyanate). A self-extinguishable rigid foam is thus developed with a creaming time of 13 seconds and a development time of 75 seconds.

The main physical and mechanical characteristics of this foam are shown in Table I and its fire-resisting properties in Table II.

EXAMPLE 10 (REFERENCE)

The operating procedure is similar to that described in Example 7, but using 100 g of commercial polyether polyol, 128 g of methylene bis(4-phenylisocyanate) and a mixture of amines comprising 1.5 g of triethylamine and 0.5 g of triethylene diamine. A combustible rigid foam is thus developed with a creaming time of 35 seconds and a development time of 85 seconds. The main physical and mechanical characteristics of this foam are shown in Table I and its fire-resisting properties in Table II.

Table I

| Example No. | 7 | | 8 | | 9 | | 10 | |
| --- | --- | --- | --- | --- | --- | --- | --- | --- |
| Characteristics of foam | | | | | | | | |
| Apparent specific gravity, kg/m³ | 36.3 | | 36 | | 32 | | 29.6 | |
| Mean dimension of cells | | | | | | | | |
| mm - horizontal direction | 0.24 | | 0.22 | | 0.32 | | 0.30 | |
| vertical direction | 0.42 | | 0.46 | | 0.46 | | 0.65 | |
| Proportion of closed cells (SCHOLTEN method), %* | 90 | | 91 | | 91 | | 88 | |
| Absorption of water (standard ASTM D 2127), vol. % | 1.8 | | 1.8 | | 2.5 | | 1.5 | |
| Thermal conductivity (according to standard DIN 5 2612) cal/cm.sec. °C. | $0.7 \times 10^{-4}$ | | $0.6 \times 10^{-4}$ | | $0.63 \times 10^{-4}$ | | $0.6 \times 10^{-4}$ | |
| Compressive strength (standard ISO R 844), kg/cm² ** | ↑↑ | ⊹ | ↑↑ | ⊹ | ↑↑ | ⊹ | ↑↑ | ⊹ |
| Stress at 10% deformation | 1.64 | 1.35 | 1.93 | 1.34 | 2.37 | ND | 1.88 | 1.16 |
| Maximum load | 1.91 | 1.35 | ND | ND | ND | ND | 1.88 | 1.16 |
| Bending strength (standard ISO R 1209)** | ↑↑ | ⊹ | | | | | ↑↑ | ⊹ |

Table I-continued

| Example No. | 7 | | 8 | 9 | 10 | |
|---|---|---|---|---|---|---|
| Breaking load, kg | 1.56 | 2.66 | ND | ND | 1.49 | 2.71 |
| Knife displacement at break, mm | 18.1 | 12.0 | ND | ND | 14.4 | 10.0 |
| Dimensional stability (at 100° C. in ambient humidity) aluminum ICI/foil method, samples of 15 × 15 × 1 cm, surface variation, α after 1 day | +5.8 | | 0 | ND | +4.7 | |
| after 7 days | +8.6 | | 0 | +4.5 | +8.3 | |
| SCHOLTEN method, samples of 5 × 5 × 5 cm, mean variation of length of edges, % after 1 day | +0.53 | | ND | ND | +0.87 | |
| after 7 days | +1.1 | | +0.5 | ND | +1.5 | |
| Friability (method ASTM C 421) Loss of weight in % after 2 mins. | 4.0 | | 2.0 | 0.7 | 4.2 | |
| after 10 mins. | 16.8 | | 11.2 | 5.2 | 26.0 | |

ND : not determined
\* : uncorrected for surface cells
\*\* ↑ ↑ indicates stresses parallel to the expansion of the foam
+ indicates stresses perpendicular to the expansion of the foam.

Table II

| Example No. | 7 | 8 | 9 | 10 (ref) |
|---|---|---|---|---|
| Inflammability test (standard ASTM D 1692) | | | | |
| Class | Self-extinguishable | Self-extinguishable | Self-extinguishable | Combustible |
| Time elapsing before extinction, sec. | 47 | 43 | 47 | — |
| Duration of combustion, sec. | — | — | — | 46 |
| Extent of combustion, cm | 2.6 | 3.3 | 3 | 12.7 |
| Extent of combustion, % | 20.5 | 25.9 | 23.5 | 100 |
| Speed of combustion, cm/min | 3.3 | 4.6 | 3.8 | 16.6 |
| Inflammability test (according to standard ASTM E 162) | | | | |
| Class | Self-extinguishable | Self-extinguishable | Self-extinguishable | Combustible |
| Time elapsing before extinction, sec. | 132 | ND | 86 | — |
| Duration of combustion, sec. | — | ND | — | — |
| Extent of combustion, cm | 17.6 | ND | 31.5 | — |
| Extent of combustion, % | 61.5 | ND | 90 | — |
| Speed of combustion, cm/min | 9.8 | ND | 22 | — |

EXAMPLE 11 (REFERENCE)

The operating procedure is similar to that described in Example 7, but using 100 g of an epichlorohydrin oligomer produced by adding 5 moles of epichlorohydrin to 1 mole of glycerine. The main characteristics of this product are as follows:

| | |
|---|---|
| Specific gravity, 20° C. | 1.347 |
| Viscosity at 20° C., poises | 232 |
| Chlorine content, % by weight | 32.41 |
| Hydroxyl index, mg KOH/g polyol | 282 |
| Gardner coloration index | 3 |
| Mean measured molecular mass | 548 |

In addition to the 100 g of oligomer described above, 0.5 g of silicone DC 193, 1.5 g of triethylamine, 30 g of trichlorofluoromethane and 71.6 g of crude methylene bis(4-phenylisocyanate) are used.

The creaming time amounts to 20 seconds.

After 101 seconds a foam has been developed which has a specific gravity of 35.8 kg/m$^3$ which is self-extinguishable according to the standards ASTM D 1692 and E 162.

The bending strength and compressive strength properties of this foam are comparable to those of the foam produced in Example 7. Nevertheless, its dimensional stability is entirely inadequate; the variations of the surface or mean length of the edges of samples of 15×15×1 cm, kept for 1 day at 100° C. in ambient humidity, are even no longer measurable because of the softening of the samples and the appearance of numerous crevices.

The comparison of the properties of the rigid polyurethane foams produced in accordance with Examples 7, 8, 9, 10, and 11 amply shows that the new chlorinated polyether polyols according to the invention permit the production of self-extinguishable rigid foams having mechanical properties comparable with if not better than those of the rigid foams produced with the aid of non-halogenated polyether polyols, particularly good dimensional stability, a property which is indispensable for the effective use of rigid foams and which is not possessed by foams produced with the aid of chlorinated polyether polyols of the prior art.

We claim:

1. Polyether polyols of the general formula:

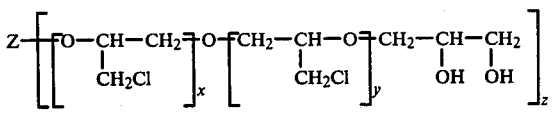

in which z represents a number between 2 and 6, x and y represent numbers between 0 and 12 such that the mean value $\overline{x+y}$ per chain is between 0 and 12, and that $z\overline{(x+y)}$ in which $\overline{\overline{x+y}}$ represents the mean value of $x+y$ in the entire molecule is between 1 and 72 and Z represents the residue of a halogenated polyhydroxyl compound initiator and comprises a $C_2$ to $C_6$ halogenated aliphatic radical of valence z, the halogen being selected from the group consisting of chlorine and bromine.

2. Polyether polyols according to claim 1 wherein Z represents the bivalent organic radical

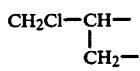

3. Polyether polyols according to claim 1 wherein the halogen of $C_2$ to $C_6$ halogenated aliphatic radical is bromine.

4. Polyether polyols according to claim 1 wherein Z represents the bivalent brominated saturated radical

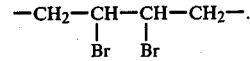

5. Polyether polyols according to claim 1 wherein Z represents the bivalent brominated unsaturated radical

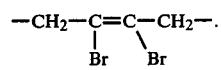

6. Polyether polyols according to claim 1 characterized in that x and y represent numbers between 0 and 4 such that the mean value $\overline{x+y}$ per chain is between 0 and 4 and that $z\overline{(x+y)}$, in which $\overline{\overline{x+y}}$ represents the mean value of $x+y$ in the entire molecule, is between 1 and 24.

* * * * *